United States Patent [19]

Spiegler et al.

[11] Patent Number: 4,824,973
[45] Date of Patent: Apr. 25, 1989

[54] PREPARATION OF 4-FORMYLTETRAHYDROPYRANS

[75] Inventors: Wolfgang Spiegler, Worms; Wolfgang Hoelderich, Frankenthal; Norbert Goetz, Worms; Leopold Hupfer, Friedelsheim; Jochen Wild, Deidesheim, all of Fed. Rep. of Germany

[73] Assignee: BASF Aktiengesellschaft, Ludwigshafen, Fed. Rep. of Germany

[21] Appl. No.: 89,752

[22] Filed: Aug. 26, 1987

[30] Foreign Application Priority Data

Sep. 9, 1986 [DE] Fed. Rep. of Germany ....... 3630614

[51] Int. Cl.$^4$ .................. C07D 309/06; C07D 333/22
[52] U.S. Cl. ..................................... 549/425; 549/60; 546/268
[58] Field of Search .................. 549/425, 60; 568/486; 546/268

[56] References Cited

U.S. PATENT DOCUMENTS 2,870,214 1/1959 Perry et al. ......................... 568/486
4,011,278 3/1977 Plank et al. ......................... 564/332
4,306,106 12/1981 Kerr et al. ............................ 568/791

OTHER PUBLICATIONS

Blanchard, Jr. et al., JACS, 85, 955 (1963).
Yvernault et al., C. A., 70, 96110e (1969).
CA 79, 66132g (1973).
CA 79, 12628e (1973).
CA 76, 25029y (1972).
CA 87, 151967t (1977).
CA 87, 23051c (1977).
CA 100, 68212j (1984).

Primary Examiner—Nicky Chan
Attorney, Agent, or Firm—John H. Shurtleff

[57] ABSTRACT

4-Formyltetrahydropyrans of the general formula I

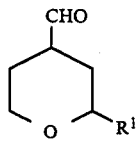

where $R^1$ is hydrogen, $C_1$–$C_{12}$-alkyl, $C_2$–$C_{12}$-alkenyl, $C_1$–$C_6$-alkoxy-substituted $C_1$–$C_{12}$-alkyl, $C_4$–$C_{12}$-cycloalkyl, unsubstituted or substituted aryl, hetaryl or aralkyl, or an unsubstituted or substituted, saturated or unsaturated 5-membered or 6-membered ring which may be interrupted by N, O or S, are prepared by a process in which a pyran derivative of the general formula II

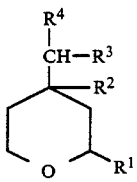

where $R^1$ is as defined above, $R^2$ and $R^3$ are each OH or together are an oxygen atom and thus form an oxirane ring, and $R^4$ is hydrogen where $R^2$ and $R^3$ are each OH, and is hydrogen or tert-butoxycarbonyl where $R^2$ and $R^3$ together are an oxygen atom, is treated at elevated temperatures with a catalyst selected from the group consisting of zeolites, phosphates, boric acid on a carrier and silica or mixtures of these. Novel 4-formyltetrahydropyrans are also proposed.

5 Claims, No Drawings

PREPARATION OF 4-FORMYLTETRAHYDROPYRANS

The present invention relates to a process for the preparation of 4-formyltetrahydropyrans.

4-Formyltetrahydropyrans and some of their alkyl derivatives are known and are prepared in the following manner.

Reaction of 4-oxotetrahydropyran with Grignard reagents obtained from alkoxymethyl halides and magnesium followed by hydrolysis to give 4-formyltetrahydropyran is described in Arm. Khim. Zh. 26 (1973), 227, CA 79, 66132 g; Dokl. Vscs. Konf. Khim. Atselinena 4th, 1972, 348, CA 79, 12628e and Arm. Khim. Zh. 24 (1971), 503, CA 76, 25029 y.

The reaction of 4-oxotetrahydropyran with the Wittig reagents alkoxymethylenetriphenylphosphoranes like-wise gives the corresponding 4-formyltetrahydropyrans (cf. Arm. Khim. Zh. 27 (1974), 945).

According to Darzens glycidyl ester method, various 4-tetrahydropyranylideneglycidyl esters were converted to the aldehydes in aqueous solution (cf. Arm. Khim. Zh. 30 (1977), 516, CA 87, 151967 t; Sint. Geterotsikl. Soedin 1979, 25, CA 94, 30479 w; Arm. Khim. Zh. 36 (1983), 597, CA 100, 68212 j; Arm. Khim. Zh. 25 (1972), 173, CA 77, 48187 k; SU-A-550 389, CA 87, 23051 c).

4-Formyltetrahydropyran was obtained by distilling spiro-1,6-dioxa[2,5]octane over zinc chloride (cf. Chem. Ber. 91 (1958), 1589). 4-Formyltetrahydropyran was also prepared from tetrahydropyran-4-carbonyl chloride by the Rosemund reduction and from 4,8-dioxabicyclo[5.1.0]octa-2,5-diene by rearrangement and subsequent catalytic hyrogenation, as described in Angew. Chemie 86 (1974), 742.

However, the stated syntheses have a number of disadvantages. The preparation of alkoxymethylmagnesium halides and alkoxymethylenetriphenylphosphoranes requires the use of halomethyl ethers. Because of their toxic properties, they are substances which are difficult to handle and which, where technically possible, should not be used. The glycidyl ester method gives maximum yields of 70%. For unsubstituted 4-formyltetrahydropyran, the yield is 36% (cf. Comparative Example 1). These poor yields make this synthesis route uneconomical. In the distillation of 1,6-dioxaspiro[2,5]octane over zinc chloride, the reaction is incomplete, and the yield of 4-formyltetrahydropyran is not stated. In fact, the yield is only about 42% (cf. Comparative Example 2). It is also stated that a solid crystalline mass having a melting point of 218°–223° C. is formed when the mixture is left to stand in a closed vessel. However, 4-formyltetrahydropyran is a colorless, readily mobile liquid at room temperature. The same applies to the Rosemund reduction of tetrahydropyran-4-carbonyl chloride. In this case too, no yields are stated and the melting point of the reaction product is given as 135° C., which means that this product too cannot be 4-formyltetrahydropyran. These solids designated as 4-formyltetrahydropyran are presumable higher molecular weight adducts of the aldehyde which, however, cannot be used for a number of subsequent reactions. 4-8-Dioxabicyclo[5.1.0]octa-2,5-diene is difficult to obtain and is complete unsuitable as a starting material for an industrial synthesis.

It is also known that the corresponding aldehydes are obtained from substituted 1,2-diols (review article in Houben-Weyl, Methoden der organischen Chemie, Volume E 3 (1983), 491), subsittuted oxiranes (review article in Houben-Weyl, Methoden der organischen Chemie, Volume E 3 (1983), 496) and substituted tert-butyl glycidyl esters (review article in Houben-Weyl, Methoden der organischen Chemie, Volume E 3 (1983), 530).

It is furthermore known that butylene oxide can be converted to 55–72% of butyraldehyde, 19–34% of cis/trans-but-2-enol, 3–9% of butanol and 2% of methyl ethyl ketone over doped A zeolites (cf. Hokkaido Dagaku Kogakubu Kenkyn Hokoku 67 (1973), 171–178). The selectivity in this reaction is unsatisfactory. Furthermore, the A zeolite catalyst cannot be regenerated after it has been deactivated by coking, since the crystal structure of this zeolite is destroyed at the temperature of about 500° C. required for this purpose.

This also applies to the preparation of 2-(4′-isobutylphenyl)-propanal from 2-(4′-isobutylphenyl)-2-methyloxirane over 5 Å molecular sieves (cf. JP-A-3031-637).

For the conversion of propylene oxide to acetone or propionaldehyde over alkali -doped X zeolites (Waseda Daigaku Rikogaku Kenkyusho Hokoku 67 (1974), 26–29), it is necessary to carry out the reaction in the absence of strongly acidic centers.

Cyclododecanone is obtained from epoxycyclododecane over Ph-doped or Rh-doped Al$_2$O$_3$ (Neftekhimiya 16 (1976), 250–254). This publication expressly points out that zeolites are unsuitable for this reaction.

EP-A-100 117 describes the reaction of styrene oxide and of styrene oxides which are alkyl-substituted or alkoxy-substituted in the aromatic nucleus over a titanium-containing zeolite to give β-phenylacetaldehydes in the liquid phase at from 30° to 100° C. The catalyst used for this purpose has to be prepared by a complicated method from expensive, very pure educts, such as tetraalkyl orthosilicates, tetraalkyl orthotitanates and tetrapropylammonium hydroxide. A high conversion is achieved only when the reaction takes place in a solvent, such as methanol or acetone, at from 30° to 100° C. in the liquid phase and residence times of from 1 to 1.5 hours are maintained. This entails increased distillation and operation costs. Furthermore, the reaction over titanium-containing zeolite is not generally applicable and is possible only in the case of styrene oxide and styrene oxides which are alkylated or alkoxylated in the aromatic nucleus.

It is an object of the present invention to provide a process for the preparation of novel and known 4-formyltetrahydropyrans, and novel 4-formyltetrahydropyrans.

We have found that this object is achieved by a process of the stated type for the preparation of 4-formyltetrahydropyrans of the general formula I

where R$^1$ is hydrogen, C$_1$–C$_{12}$-alkyl, C$_2$–C$_{12}$-alkenyl, C$_1$–C$_6$-alkoxy-substituted C$_1$–C$_{12}$-alkyl, C$_4$–C$_{12}$-cycloalkyl, unsubstituted or substituted aryl, hetaryl or aralkyl, or an unsubstituted or substituted, saturated or unsaturated 5-membered or 6-membered ring which may be interrupted by N, O or S, wherein a pyran derivative of the general formula II

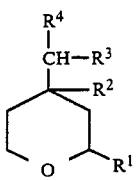
(II)

where $R^1$ is as defined above, $R^2$ and $R^3$ are each OH or together are an oxygen atom and thus form an oxirane ring, and $R^4$ is hydrogen where $R^2$ and $R^3$ are each OH, and is hydrogen or tert-butoxycarbonyl where $R^2$ and $R^3$ together are an oxygen atom, is treated at elevated temperatures with a catalyst selected from the group consisting of zeolites, phosphates, boric acid on a carrier and silica and mixtures of these.

The novel 4-formyltetrahydropyrans are of the general formula I'

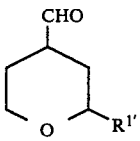
(I')

where $R^{1'}$ is $C_4$-$C_{12}$-alkyl, $C_4$-$C_{12}$-cycloalkyl, $C_1$-$C_6$-alkoxy-substituted $C_1$-$C_{12}$-alkyl, hetaryl or aryl which is unsubstituted or substituted by $C_1$-$C_6$-alkoxy, halogen or trifluoromethyl, aralkyl where alkyl is of 1 to 6 carbon atoms, or a 5-membered or 6-membered, saturated or unsaturated ring which is interrupted by one or more N, O or S atoms.

The pyran derivatives used as starting compounds of the general formula II are of the following general formulae II a, II b and II c

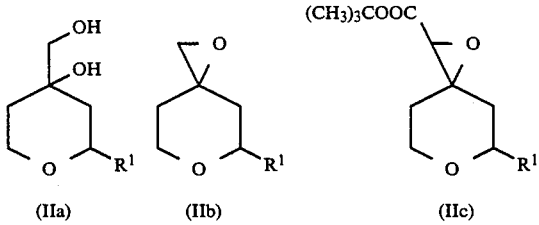

(IIa)  (IIb)  (IIc)

where $R^1$ has the meanings stated at the outset.

In the novel process, it is preferable to use 4-hydroxy-4-hydroxylmethyl-tetrahydropyran or 1,5-dioxaspiro[2,6]octane as the starting compound of the general formula II.

If $R^1$ in the general formula I is $C_1$-$C_{12}$-alkyl, it is, in particular, methyl, ethyl, n-propyl, isopropyl, n-butyl, isobutyl, pentyl, hexyl, octyl, decyl or dodecyl. The $C_1$-$C_{12}$-alkyl radicals may be straight-chain or branched.

Where $R^1$ is $C_2$-$C_{12}$-alkenyl, it is, for example, ethenyl, propenyl, butenyl or pentenyl. The $C_1$-$C_{12}$-alkyl radical can, if desired, be substituted by $C_1$-$C_6$-alkoxy. Particularly suitable alkoxy radicals are methoxy, ethoxy, propoxy and butoxy. $R^1$ may furthermore be $C_4$-$C_{12}$-cycloalkyl, eg. cyclobutyl, cyclopropyl, cyclohexyl, cyclooctyl or cyclododecyl.

$R^1$ is furthermoe unsubstituted or substituted aryl, hetaryl or aralkyl. Suitable substituents here are the conventional ones, in particular $C_1$-$C_6$-alkyl, halogen, in particular fluorine, chlorine and bromine, and $C_1$-$C_6$-alkoxy. Examples of aryl, hetaryl and aralkyl radicals are, in particular, phenyl, naphthyl, pyridyl, thienyl, furyl, benzyl or phenylethyl.

$R^1$ may also be an unsubstituted or substituted, saturated or unsaturated 5-membered or 6-membered ring which may be interrupted by N, O or S. In particular, tetrahydropyranyl, furanyl and morpholinyl may be mentioned here.

In general formula I', $R^{1'}$ is $C_4$-$C_{12}$-alkyl, eg. butyl, pentyl, hexyl, octyl, decyl or dodecyl. It may furthermore be $C_4$-$C_{12}$-cycloalkyl and have the meanings given in explaining the possible meanings of $R^1$. The same applies to the possible meanings of $C_1$-$C_6$-alkoxy-substituted $C_1$-$C_{12}$-alkyl and the remaining possible meanings of $R^{1'}$.

The novel process has a number of advantages over the known syntheses of 4-formyltetrahydropyrans. For example, 4-formyltetrahydropyran was obtained for the first time from readily available, cheap starting materials in high yield and in the monomeric form, which is very important for subsequent reactions. Furthermore, it is possible to dispense with the use of the toxic halomethyl ethers for the preparation of the Gignard or Wittig reagents for the reaction with 4-oxotetrahydropyrans, the said halomethyl ethers being difficult to handle. The yields in the reaction of the tert-butyl glycidyl esters II c are substantially higher than those obtained to date in the preparation of 4-formyltetrahydropyrans from glycidyl esters.

When the zeolite catalysts used in the novel process are employed, excellent yields, selectivities and catalyst lives are obtained. This is all the more surprising when it is considered that the reactions are advantageously carried out at elevated temperatures in the gas phase and the sensitive 4-formyltetrahydropyrans are not decomposed by the acidic zeolites in spite of their cracking properties.

The catalysts used according to the invention are readily available, have high activity and are easily regenerated (the initial activity is retained). Furthermore, high conversions, high selectivities and flexible use of the catalyst with regard to the educts are ensured, in conjunction with long catalyst lives.

The novel process avoids the disadvantages of the conventional procedures, stated at the outset. In view of the prior art, the success of the process is all the more surprising since to date only weakly acidic X zeolites were used, or zeolites were considered unsuitable for rearrangement reactions. Hence, it could not be expected that such excellent results would be obtained in such wide limits and with such a great variety of educts precisely with zeolites which possess high acidity and rigid structural parameters.

The advantages of the novel process for the rearrangement over the catalysts according to the invention are: complete conversion, no separation problems, long catalyst lives, high selectivities, also very good yields in the case of starting materials substituted in the aromatic nucleus, simple isolation of the end products, as a rule further use without additional purification, and easy regeneration of the catalysts in the event of coking. Another advantage is the fact that the reaction can be carried out in the gas phase, which is preferred.

In summary, the novel process is accordingly more economical and technically simpler to carry out than the known syntheses, and gives 4-formyltetrahydropyrans in higher yields and purity than hitherto.

The starting compounds of the general formula II can be obtained by a conventional method from the corresponding 4-methylenetetrahydropyrans by oxidation to the diols (II a) (Khim. Geterotsikl. Soedin. 1983, 891) or to the oxiranes (II b) (Izv. Akad. Nauk. SSSR, Ser. Khim. 1982, 2114) or from the corresponding 4-oxotetrahydropyrans by reaction with tert-butyl chloroacetate to give the glycidyl esters (II c). The 4-methylenetetrahydropyrans used are prepared by reacting 3-methyl-3-buten-1-ol with an aldehyde of the general formula (III)

$$R^1-CHO \qquad (III),$$

where $R^1$ is as defined above, as described in, for example, Arm. Khim. Zh. 29 (1976), 1033, CA 87, 5757 h, and can be purified by subsequent distillation. The diastereomer pair obtained is used, without being separated, in the rearrangement reaction to give the diastereomer mixture of the aldehyde I.

The abovementioned compounds are a selection of useful components for the preparation of aldehydes of the general formula I and are not intended to restrict the range of use of the novel process for a wide variety of aldehydes of the formula I.

Acidic zeolite catalysts are advantageously used as catalysts for the novel conversion. Zeolites are crystalline aluminosilicates which have a highly ordered structure comprising a rigid three-dimensional network of $SiO_4$ and $AlO_4$ tetrahedra which are linked by common oxygen atoms. The ratio of Si and Al atoms to oxygen is 1:2 (cf Ullmanns Encyclopädie der techn. Chemie, 4th Edition, Volume 24, page 575 (1983)). The electrovalency of the aluminum-containing tetrahedra is compensated by the inclusion of cations in the crystal, eg. an alkali metal or hydrogen ion. Cation exchange is possible. The voids between the tetrahedra are occupied by water molecules prior to dehydration by drying or calcination.

In the zeolites, other trivalent and divalent elements, such as B, Ga, Fe, Cr, Be, As, Sb and Bi, or mixtures of these can be incorporated in the lattice in place of aluminum, or the silicon can be replaced by a tetravalent element, such as Ge, Ti, Zr or Hf.

Suitable catalysts are zeolites of the mordenite group or faujasite group, such as L zeolites or fine-pored zeolites of the erionite or chabasite type. Particularly advantageous for the novel process are zeolites of the pentasil type. These zeolites can have different chemical compositions and are aluminosilicate, borosilicate, iron silicate, gallium silicate, chromium silicate, beryllium silicate, arsenic silicate, antimony silicate and bismuth silicate zeolites or mixtures of these, and aluminogermanate, borogermanate, gallium germanate and iron germanate zeolites or mixtures of these.

The aluminosilicate, borosilicate and iron silicate zeolites of the pentasil type are particularly useful for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in 1,6-hexanediamine or 1,3-propanediamine or triethylenetetramine solution, with or, in particular, without the addition of an alkali or alkaline earth, at from 100° to 220° C. under autogenous pressure. These zeolites also include the isotactic zeolites according to DE-A-3 006 471 and EP-A-46 504. The aluminosilicate zeolites obtained have an $SiO_2/Al_2O_3$ ratio of from 10 to 40,000, depending on the choice of the amounts of starting materials. Such aluminosilicate zeolites can also be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These zeolites also include the isotactic zeolites according to DE-A-3 006 471 and EP-A-46 504. Such borosilicate zeolites can also be prepared if the reaction is carried out in ether solution, eg. diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogenous pressure.

After they have been isolated, dried at from 100° to 160° C., preferably 110° C., and calcined at from 450° to 550° C., preferably from 500° to 540° C., the aluminosilicate, borosilicate and iron silicate zeolites thus prepared can be molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried for 16 hours at 110° C. and calcined for 16 hours at 500° C.

Advantageous catalysts are also obtained if the isolated aluminosilicate or borosilicate zeolite is molded directly after being dried and is subjected to calcining only after the molding procedure. The aluminosilicate and borosilicate zeolites prepared can be used in pure form, without a binder, as extrudates or pellets, the extrudation or peptizing assistants used being, for example, ethylcellulose, stearic acid, potato starch, formic acid, oxalic acid, acetic acid, nitric acid, ammonia, amines, silicoesters and graphite or mixtures of these.

If, because of the manner of its preparation, the zeolite is not in the catalytically active, acidic H form but, for example, in the Na form, the latter can be converted completely or partially to the desired H form by ion exchange, for example with ammonium ions, and subsequent calcination, or by treatment with an acid.

If, when the zeolite catalysts are used according to the invention, deactivation takes place as a result of coking, it is advisable to regenerate the zeolites by burning off the coke deposit with air or with an air/$N_2$ mixture at from 400° to 550° C., preferably from 500° to 540° C. As a result, the zeolites attain their initial activity again. By precoking it is possible to adjust the activity of the catalyst to provide optimum selectivity with respect to the desired reaction product.

In order to achieve very high selectivity, high conversion and a long catalyst life, it is sometimes advantageous to modify the zeolites. In a suitable method for modifying the catalysts, for example, the unmolded or molded zeolites are doped with metal salts by ion exchange or impregnation.

Advantageously, doping is carried out, for example, by initially taking the molded pentasil zeolite in a riser tube and passing, for example, an aqueous or ammoniacal solution of a halide or nitrate of the metals over the zeolite at from 20° to 100° C. Ion exchange of this type can be carried out, for example, over the hydrogen, ammonium and alkali metal form of the zeolite. In another possible method of applying the metals to the zeolite, the zeolite material is impregnated, for example with a halide, a nitrate or an oxide of the metals in aqueous, alcoholic or ammoniacal solution. Both ion exchange and impregnation are followed at least by a drying step and, if desired, by repeated calcination.

In a possible embodiment, for example, $Cs_2CO_3$ is dissolved in water. This solution is used to impregnate the molded or unmolded zeolite for a certain time, for example about 30 minutes. Any supernatant solution is freed from water in a rotary evaporator. The impregnated zeolite is then dried at about 150° C. and calcined at about 550° C. This impregnation process can be carried out several times in succession in order to obtain the desired metal content.

It is also possible, for example, to prepare an ammoniacal $Pd(NO_3)_2$ solution and to suspend the pure zeolite powder therein at from 40° to 100° C. for about 24 hours, while stirring. After the zeolite material obtained in this manner has been filtered off, dried at about 150° C. and calcined at about 500° C., it can be further processed with or without a binder to give extrudates, pellets or fluidizable material.

Ion exchange of the zeolite in the H form can be carried out as follows: the zeolite in the form of extrudates or pellets is initially taken in a column, and, for example, an ammoniacal $Pd(NO_3)_2$ solution is circulated over the said zeolite at slightly elevated temperatures of from 30° to 80° C. for from 15 to 20 hours. The product is then washed thoroughly with water, dried at about 150° C. and calcined at about 550° C.

In the case of some metal-doped zeolites, after-treatment with hydrogen is advantageous.

In another possible method of modification, the molded or unmolded zeolite material is subjected to a treatment with acids, such as hydrochloric acid, hydrofluoric acid and phosphoric acid, and/or steam.

The silicon-rich zeolites which may be used (molar ratio $SiO_2/Al_2O_3 \geq 10$) include known ZSM types as well as ferrierite and Nu-1 and Silicalit ®, a molecular sieve or a silica polymorph.

Other catalysts for the preparation of aldehydes of the general formula I from appropriate epoxides of the general formula II are described below.

In particular, aluminum phosphates synthesized under hydrothermal conditions are used as aluminum phosphate catalysts for the novel process.

Examples of aluminum phosphates prepared under hydrothermal conditions are APO-5, APO-9, APO-11, APO-12, APO-14, APO-21, APO-25 and APO-33. Syntheses of these compounds are described in EP-A-No. 132 708, US-A-No. 4 310 440 and US-A-No. 4 473 663.

For example, $AlPO_4$-5 (APO-5) is synthesized by homogeneously mixing orthophosphoric acid with pseudoboehmite (Catapa ®SB) in water, adding tetrapropylammonium hydroxide to this mixture and then reacting the components at about 150° C. for 20-60 hours under autogenous pressure in an autoclave. The $AlPO_4$-5 filterd off is dried at 100°-160° C. and calcined at 450°-550° C.

$AlPO_4$-9 (APO-9) is likewise synthesized from orthophosphoric acid and pseudoboehmite, but in aqueous DABCO (1,4-diazabicyclo[2.2.2]octane) solution at about 200° C. under autogenous pressure for 200-400 hours.

$AlPO_4$-21 (APO-21) is synthesized from orthophosphoric acid and pseudoboehmite in aqueous pyrrolidone solution at 150°-200° C. under autogenous pressure for 50-200 hours.

The silicon aluminum phosphates used for the novel process are, for example, SAPO-5, L SAPO-11, SAPO-31 and SAPO-34. The synthesis of this compound is described in, for example, EP-A-No. 103 117 and US-A-No. 4 440 871. SAPOs are prepared by crystallization from an aqueous mixture at 100°-250° C. and under autogenous pressure in the course of 2 hours, the reaction mixture of a silicon, an aluminum and a phosphorus component being reacted in an aqueous solution of an organic amine.

For example, SAPO-5 is obtained by mixing $SiO_2$, suspended in aqueous tetrapropylammonium hydroxide solution, with an aqueous suspension of pseudoboehmite and orthophosphoric acid and then reacting the components at 150°-200° C. for 20-200 hours under autogenous pressure in a stirred autoclave. The powder filtered off is dried at 110°-160° C. and calcined at 450°-550° C.

Examples of suitable silicon aluminum phosphates are ZYT-5, ZYT-6, ZYT-7, ZYT-9, ZYT-11, and ZYT-12 (JP-A-No. 5 9217-619).

Boron phosphates for the novel process can be prepared, for example, by mixing and kneading concentrated boric acid and phosphoric acid followed by drying and calcination in an inert gas, air or steam atmosphere at 250°-650° C., preferably 300°-500° C.

Other suitable phosphates for the novel process are $CePO_4$, $FePO_4$, $SrHPO_4$ and $Zr_3(PO_4)_4$.

Other catalysts used for the novel process are phosphoric acid or boric acid on $SiO_2$, $Al_2O_3$ or pumice carriers, applied, for example, by impregnation or spraying. A catalyst containing phosphoric acid can be obtained, for example, by impregnating $SiO_2$ with $H_3PO_4$, $NaH_2PO_4$ or $Na_2HPO_4$ solution and then drying and calcining the product. However, it is also possible to spray phosphoric acid together with the silica gel in a spray tower; this is followed by drying and generally calcination. Phosphoric acid can also be sprayed onto the carrier in an impregnating mill. It is also possible to use silica as the catalyst.

The catalysts described here can be used alternatively in the form of 2-4 mm extrudates, pellets having a diameter of 3-5 mm, powders having particle sizes of 0.1-0.5 mm or fluidizable catalyst.

In the gas phase, which is preferred, the reaction conditions generally selected for the novel conversion of the epoxides are 150°-500° C., preferably 200°-400° C., and a WHSV of from 0.1 to 20 $h^{-1}$, preferably from 0.5 to 5 $h^{-1}$ (g of epoxide per g of catalyst per hour). In general, the conversion increases sharply with increasing temperature, while the selectivity decreases only slightly in a particular temperature range.

It is also possible to carry out the reaction in the liquid phase (suspension, trickle-bed or liquid phase procedure).

As a rule, the process is carried out under atmospheric pressure or, depending on the volatility of the starting compound, under reduced or superatmospheric pressure, either batchwise or, preferably, continuously.

Sparingly volatile or solid educts are reacted in dissolved form, for example in solution in tetrahydrofuran, toluene or petroleum ether. In general, dilution with solvents, for example as mentioned above, or inert gases such as $N_2$ or Ar is also possible.

After the reaction, the resulting tetrahydropyrans are isolated from the reaction mixture by conventional techniques, for example distillation; unconverted educts are, if required, recycled to the reaction according to the invention. Because of the very high yields, the reaction products can be directly further processed. In the novel process, the monomeric compounds are preferentially obtained.

The novel pyrans of the general formula I are useful intermediates for the synthesis of crop protection agents, drugs or dyes. Particular examples are herbicides based on cyclohexanedione, as described in, for example, DE-A-No. 3 121 355.

The compounds obtainable by the novel process can, for example, readily be further processed by methods familiar to the skilled worker, for example, by oxidation with oxygen or by reduction, for example by catalytic hydrogenation or hydrogenation under aminating conditions, to give amines, alcohols and acids, which in turn are useful intermediates.

The Examples which follow illustrate the invention.

EXAMPLES 1–34

The reactions are carried out under isothermal conditions in a tube reactor (0.6 cm coil, 90 cm long) in the gas phase in the course of not less than 6 hours. Separation and characterization of the reaction products was effected by conventional methods. Quantitative determination of the reaction products and the starting substances was effected by gas chromatography and by means of the CO number.

The catalysts used in the Examples for the novel process are:

CATALYST A

The aluminosilicate zeolite of the pentasil type was prepared under hydrothermal conditions from 650 g of finely divided $SiO_2$ and 203 g of $Al_2(SO_4)_3 \cdot 18H_2O$ in 10 kg of an aqueous 1,6-hexanediamine solution (mixture, 50:50% by weight) in a stirred autoclave under autogenous pressure and at 150° C. The crystalline reaction product was filtered off, washed thoroughly, dried for 24 hours at 110° C. and then calcined for 24 hours at 500° C. This aluminosilicate zeolite contains 82.8% by weight of $SiO_2$ and 4.2% by weight of $Al_2O_3$.

Catalyst A is obtained by molding the pure aluminosilicate zeolite of the pentasil type with molding assistants to give 2 mm extrudates, drying the latter for 16 hours at 110° C. and calcining them for 24 hours at 500° C.

CATALYST B

The borosilicate zeolite of the pentasil type is prepared in a hydrothermal synthesis from 640 g of finely divided $SiO_2$, 122 g of $H_3BO_3$ and 8 kg of an aqueous 1,6-hexanediamine solution (mixture, 50:50% by weight) at 170° C. under autogenous pressure in a stirred autoclave. The crystalline reaction product is filtered off, washed thoroughly, dried for 24 hours at 100° C. and then calcined for 24 hours at 500° C. This borosilicate zeolite is composed of 94.2% by weight of $SiO_2$ and 2.3% by weight of $B_2O_3$.

This material is used to prepare 2 mm extrudates by molding with molding assistants, and the extrudates are dried for 16 hours at 110° C. and calcined for 24 hours at 500° C.

CATALYST C

Catalyst C is obtained by impregnating catalyst B with aqueous $Cu(NO_3)_2$ solution. After repeated drying and calcination for 2 hours at 540° C., the Cu content is 3.4% by weight.

CATALYST D $AlPO_4$-9 (APO-9) is synthesized by dissolving 200 g of 98% strength phosphoric acid, and suspending 136 g of boehmite, in 400 g of water, adding an aqueous solution of 112 g of diazabicyclo[2.2.2]octane (DABCO) and 320 g of $H_2O$, and reacting this mixture in a stirred autoclave at 200° C. for 336 hours under autogenous pressure. The crystalline material is filtered off, dried at 120° C. and then calcined for 16 hours at 500° C. The $AlPO_4$-9 synthesized in this manner contains 49.0% by weight of $P_2O_5$ and 37.1% by weight of $Al_2O_3$. This material is molded with extrusion assistants to give 3 mm extrudates, which are repeatedly dried at 120° C. and calcined for 6 hours at 500° C.

CATALYST E

Silicon aluminum phosphate-5 (SAPO-5) is prepared from a mixture of 200 g of 98% strength phosphoric acid, 136 g of boehmite, 60 g of 30% strength silica sol, 287 g of tripropylamine and 587 g of $H_2O$. This mixture is reacted at 150° C. for 168 hours under autogenous pressure. The crystalline product is filtered off, dried at 120° C. and then calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

CATALYST F $SiO_2$, commercially available under the trade name D11-11 from BASF AG.

The experimental results and reaction parameters are summarized in the Tables below.

TABLE 1

| Example no. | 1 | 2 | 3 | 4 | 5 | 6 | 7 |
|---|---|---|---|---|---|---|---|
| Starting material of the following formula | III' | III' | III' | IV' | IV' | V' | V' |
| Catalyst | A | B | F | B | F | A | B |
| Temperature | 300° C. | 300° C. | 300° C. | 300° C. | 300° C. | 300° C. | 300° C. |
| WHSV | $2\,h^{-1}$ | $2\,h^{-1}$ | $2\,h^{-1}$ | $3\,h^{-1}$ | $3\,h^{-1}$ | $2\,h^{-1}$ | $2\,h^{-1}$ |

TABLE 1-continued

| Example no. | 1 | 2 | 3 | 4 | 5 | 6 | 7 |
|---|---|---|---|---|---|---|---|
| Conversion % | 100 | 100 | 100 | 100 | 100 | 100 | 100 |
| Selectivity % | 97.6 | 96.6 | 96.5 | 96.0 | 93.0 | 91.8 | 91.6 |
| Yield % 4-formyltetrahydropyran | 97.6 | 96.6 | 96.5 | 96.0 | 93.0 | 91.8 | 91.6 |

III' =  O dissolved in the THF in a weight ratio of 50:50

IV' = 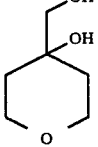 OH dissolved in THF in a weight ratio of 50:50

V' = 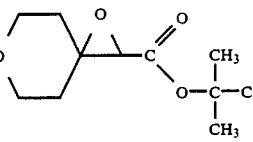 dissolved in THF in a weight ratio of 50:50

TABLE 2

| Example no. | $R^1$ IIb ($R^4$ = H; $R^3$ + $R^2$ = —O—) | Catalyst | Yield of I % | Boiling point °C./mbar |
|---|---|---|---|---|
| 8 | ethyl | B | 59 | 80–82/22 |
| 9 | i-propyl | B | 42 | |
| 10 | i-propyl | F | 66 | 79–84/14 |
| 11 | i-butyl | A | 72 [(50 + 22)$^1$] | 44–46/0.1 |
| 12 | i-butyl | B | 83 [(70 + 13)$^1$] | 79–84/14 |
| 13 | i-butyl | F | 76 [(56 + 20)$^1$] | 44–46/01 |
| 14 | n-octyl | A | 68 [(46 + 21)$^1$] | |
| 15 | n-octyl | C | 77 [(50 + 27)$^1$] | |
| 16 | cyclododecyl | B | 67 (36 + 31)$^1$ | 130–140/0.01 |
| 17 | methoxymethyl | B | 57 | |
| 18 | methoxymethyl | F | 57 | 64–68/1.0 |
| 19 | 4-tetrahydropyranyl | A | 56 | |
| 20 | 4-tetrahydropyranyl | B | 51 | 172–180/0.5 |
| 21 | 4-tetrahydropyranyl | F | 32 | |
| 22 | phenyl | A | | |
| 23 | phenyl | B | 76 (48 + 28)$^1$ | 102/0.1 |
| 24 | 4-methoxyphenyl | A | 70 | |
| 25 | 4-methoxyphenyl | B | | |
| 26 | 2-chlorophenyl | A | | |
| 27 | 2-chlorophenyl | B | 69 | |
| 28 | 3-trifluormethylphenyl | B | 73 (50 + 23)$^1$ | 95–102/0.07 |
| 29 | 2-furanyl | B | 49 | |
| 30 | 2-furanyl | F | 41 | — |
| 31 | 3-tetrahydropyranyl | B | 55 | |
| 32 | benzyl | B | 62 | |
| 33 | 4-fluorphenyl | B | 65 | |
| 34 | 4-fluorphenyl | A | | |

$^1$cis/trans isomers of I (not assigned).

COMPARATIVE EXAMPLE 1

82.1 g of 20% strength aqueous hydrochloric acid are added dropwise to a solution of 81 g of 2-sodiumcarboxyl-spiro-1,6-dioxa[2,5]octane in 500 ml of water in the course of 4 hours at 80°–85° C., after which the mixture is stirred for 30 minutes at 85° C. Steam distillation is then carried out for 3 hours. The resulting distillate (about 2 liters) is saturated with sodium chloride and extracted seven times with methylene chloride. The organic phase is dried over Na$_2$SO$_4$, and the solvent is distilled off. Distillation of the residue gives 18.1 g (36%) of 4-formyltetrahydropyran.

COMPARATIVE EXAMPLE 2

A mixture of 20 g of spiro-1,6-dioxa[2,5]octane and 0.3 g of zinc chloride is heated to 250° C. 15.2 g of a liquid are distilled off in the course of 1 hour; gas chromatographic determination shows that this liquid consists of 6.7 g (33%) of spiro-1,6-dioxa[2,5]octane and 8.5 g (42%) of 4-formyltetrahydropyran. 5.1 g of 4-formyltetrahydropyran are obtained from this liquid by distillation. On standing at room temperature, the initially clear liquid crystallizes to a colorless solid.

The starting material V' is prepared as follows: 147.8 g of potassium tert-butylate are added a little at a time to a mixture of 179.5 g of tert-butyl chloroacetates, 120 g of 4-oxotetrahydropyran and 1200 ml of tert-butanol at 10°–15° C., and the mixture is stirred for 24 hours at room temperature. The solvent is distilled off and 500 ml of water are added to the residue. The mixture is then extracted with methyl tert-butyl ether, and the organic phase is dried over Na$_2$SO$_4$ and evaporated down. The residue is distilled under reduced pressure.

Boiling point: 74° C./0.2 mbar Yield: 210 g (81% of theory) of 2-tert-butoxycarbonylspiro-1,6-dioxa[2,5]octane

We claim:

1. A process for the preparation of a 4-formyltetrahydropyran of the formula

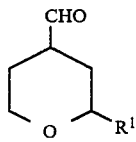

(I)

where R$^1$ is hydrogen, C$_1$–C$_{12}$-alkyl, C$_2$–C$_{12}$-alkenyl, C$_1$–C$_6$-alkoxy-substituted C$_1$–C$_{12}$-alkyl, C$_4$–C$_{12}$-cycloalkyl, unsubstituted or substituted aryl, aralkyl, or a tetrahydropyranyl ring, which process comprises:

treating a pyran derivative of the formula

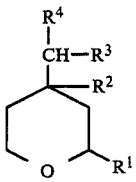

(II)

where R$^1$ is as defined above, R$^2$ and R$^3$ are each OH or together are an oxygen atom and thus form an oxirane ring, and R$^4$ is hydrogen when R$^2$ and R$^3$ are each OH, and is hydrogen or tert-butoxycarbonyl when R$^2$ and R$^3$ together are an oxygen atom, at elevated temperatures with a catalyst selected from the group consisting of zeolites, silica and mixtures thereof.

2. A process for the preparation of a 4-formyltetrahydropyran of the formula

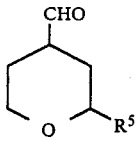

(III)

where R$^5$ is hydrogen, unsubstituted or C$_1$–C$_4$-alkoxy-substituted C$_1$–C$_{12}$-alkyl, C$_4$–C$_{12}$-cycloalkyl, phenyl which is unsubstituted or substituted by halogen or halomethyl, or benzyl, pyridyl, thienyl, furanyl or tetrahydropyranyl, wherein a pyran derivative of the formula

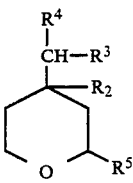

(IV)

where R$^2$, R$^3$ and R$^4$ have the meanings stated in claim 1 and R$^5$ has the abovementioned meanings, is treated at from 150° to 500° C. with a zeolite catalyst.

3. A process as claimed in claim 1, wherein 4-hydroxy-4-hydroxylmethyl-tetrahydropyran or 1,6-dioxaspiro[2,5]octane is used as the starting compound of the formula II.

4. A process as claimed in claim 1, wherein the catalyst used is a zeolite of the pentasil type, a borosilicate, iron silicate or aluminosilicate zeolite, an aluminosilicate zeolite of the faujasite, mordenite or erionite/chabacite type or a zeolite doped with alkali or alkaline earth metals or transition metals or rare earth metals.

5. A process as claimed in claim 1, which is carried out in the gas phase.

* * * * *